United States Patent
Senetar

(10) Patent No.: US 10,662,131 B2
(45) Date of Patent: May 26, 2020

(54) PROCESS FOR BUTADIENE PRODUCTION VIA OXIDATIVE DEHYDROGENATION FOLLOWED BY DIRECT DEHYDROGENATION

(71) Applicant: UOP LLC, Des Plaines, IL (US)

(72) Inventor: John J. Senetar, Naperville, IL (US)

(*) Notice: Subject to any disclaimer, the term of this patent is extended or adjusted under 35 U.S.C. 154(b) by 0 days.

(21) Appl. No.: 16/207,010

(22) Filed: Nov. 30, 2018

(65) Prior Publication Data

US 2019/0100478 A1 Apr. 4, 2019

Related U.S. Application Data

(63) Continuation of application No. PCT/US2017/038284, filed on Jun. 20, 2017.

(60) Provisional application No. 62/356,759, filed on Jun. 30, 2016.

(51) Int. Cl.
*C07C 5/48* (2006.01)
*C07C 5/333* (2006.01)

(52) U.S. Cl.
CPC ............ *C07C 5/48* (2013.01); *C07C 5/333* (2013.01); *C07C 2523/28* (2013.01); *C07C 2523/31* (2013.01); *C07C 2523/745* (2013.01)

(58) Field of Classification Search
CPC ....... C07C 5/333; C07C 5/48; C07C 2523/28; C07C 2523/31; C07C 2523/745
See application file for complete search history.

(56) References Cited

U.S. PATENT DOCUMENTS

2007/0161842 A1\* 7/2007 Johann .................... C07C 5/327
585/658
2014/0309470 A1\* 10/2014 Park ....................... B01J 23/626
585/660

\* cited by examiner

*Primary Examiner* — In Suk C Bullock
*Assistant Examiner* — Jason Y Chong

(57) ABSTRACT

A process is presented for the production of butadiene from a mixture of butane/butene feed. The process provides high conversion of the feed by oxidative dehydrogenation of the feed. The process enables recovery of a good portion of heat inputted from the reaction effluent. The process overcomes equilibrium limitations by oxidative dehydrogenation of butane/butene feed to produce butadiene.

18 Claims, 1 Drawing Sheet

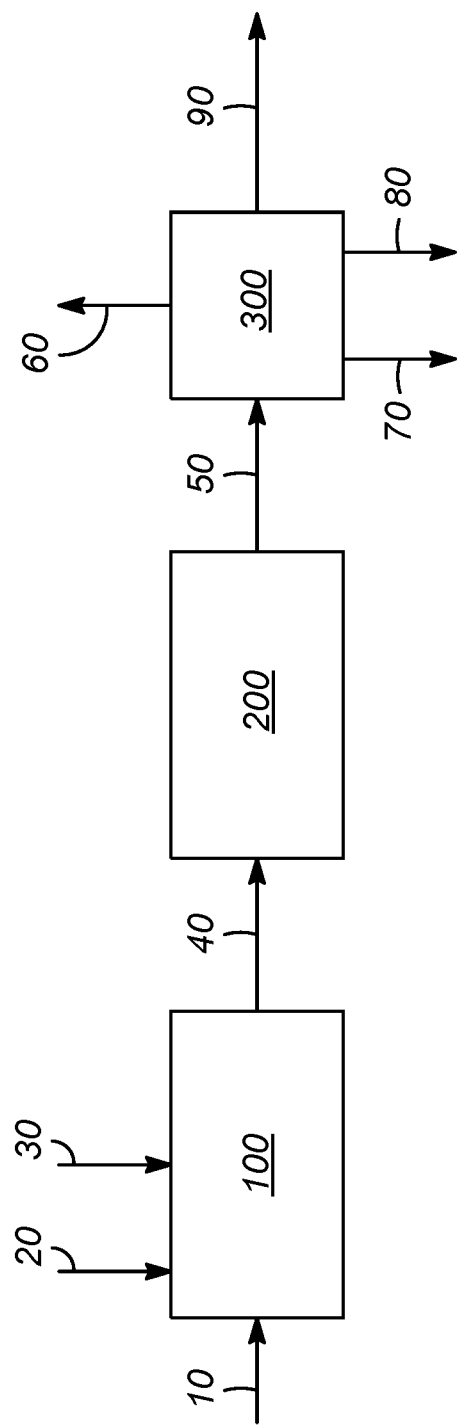

PROCESS FOR BUTADIENE PRODUCTION VIA OXIDATIVE DEHYDROGENATION FOLLOWED BY DIRECT DEHYDROGENATION

CROSS-REFERENCE TO RELATED APPLICATIONS

This application is a Continuation of copending International Application No. PCT/US2017/038284 filed Jun. 20, 2017, which application claims priority from U.S. Provisional Application No. 62/356,759 filed Jun. 30, 2016, the contents of which cited applications are hereby incorporated by reference in their entirety.

FIELD

The field of this invention relates to the production of butadiene from mixed butane/butane by oxidative dehydrogenation followed by direct dehydrogenation.

BACKGROUND

Butadiene is a basic chemical component for the production of a range of synthetic rubbers and polymers, as well as the production of precursor chemicals for the production of other polymers. Examples include homopolymerized products such as polybutadiene rubber (PBR), or copolymerized butadiene with other monomers, such as styrene and acrylonitrile. Butadiene is also used in the production of resins such as acrylonitrile butadiene styrene. Butadiene is typically recovered as a byproduct from the cracking process, wherein the cracking process produces light olefins such as ethylene and propylene. With the increase in demand for rubbers and polymers having the desired properties of these rubbers, an aim to improving butadiene yields from materials in a petrochemical plant will improve the plant economics.

Butadiene is produced almost entirely as a byproduct of ethylene plants. As ethylene plants switch from naphtha feedstock to cheaper ethane, the amount of butadiene byproduct decreases. A supply shortage is anticipated. Butadiene is mainly prepared by thermal cracking made of saturated hydrocarbons, usually naphtha being the raw material. On cracking of naphtha, a hydrocarbon mixture of methane, ethane, ethene, acetylene, propane, propylene, propyne, butenes and butadiene. A disadvantage of generation of butadiene by cracking process is formation of larger amounts of undesired coproducts. Generally, the butadiene has to be separated from butynes and other hydrocarbons formed on cracking by distillation or extraction. The production of butadiene in a cracking process inevitably falls, larger amounts of ethene or propene as coproducts. The shift from naphtha cracking to ethane cracking decreases the amount of the byproduct butadiene production. Alternatively, butadiene can be produced from n-butane by catalytic dehydrogenation.

Dehydrogenation of butane to butene followed by butene to butadiene produces hydrogen. The conversion in this process is limited by equilibrium, and positive free energy is formed by dehydrogenation reactions of butane to butene followed by butene to butadiene. The direct dehydrogenation reactions are endothermic and require additional heat input to drive the reaction. Direct dehydrogenation is slightly favorable only at high temperatures of about 700° C. There is also a low butadiene yield by this method, as in the catalytic dehydrogenation of n-butane predominantly 1-butene and 2-butene are formed.

Therefore, there is a need for a new process configuration to produce butadiene in an economical way that does not involve the additional separation processes. There is a need for an improved process for production of increased yields of butadiene.

SUMMARY

An embodiment of the invention is a process for the production of butadiene comprising passing a feed stream comprising butanes and butenes to an oxidative dehydrogenation reaction unit to generate an effluent stream comprising butanes, butenes and butadiene. The effluent stream is passed to a dehydrogenation unit to generate a process stream comprising butadiene.

Another embodiment of the invention is a process for the production of butadiene comprising passing a feed stream comprising butanes and butenes to an oxidative dehydrogenation reaction unit to generate an effluent stream comprising butanes, butenes and butadiene. Steam and oxygen are passed along with the feed stream to the oxidative dehydrogenation reaction unit. The effluent stream is passed to a dehydrogenation unit to generate a process stream comprising butadiene. The process stream is passed to a heat and product recovery unit to generate a crude C4 product stream.

The present invention seeks to provide an improved process for production of butadiene by oxidative dehydrogenation that is not equilibrium limited. The process overcomes equilibrium limitations by oxidative dehydrogenation of butane/butene feed to produce butadiene. The present invention advantageously provides a method to attain high conversion of mixed butane/butene feed to butadiene in a single pass and in addition, the high capital and energy intensive step of heating the feed to direct dehydrogenation are eliminated or minimized. These and other features, aspects, and advantages of the present invention will become better understood upon consideration of the following detailed description, drawings and appended claims.

BRIEF DESCRIPTION OF THE DRAWING

The FIGURE is a flow scheme for the process of the present invention.

DETAILED DESCRIPTION

The cracking of naphtha to ethane decreases the amount of byproduct butadiene production. The dehydrogenation of butane to butene and butene to butadiene produces hydrogen and requires a large amount of diluent steam. Traditionally, the steam is produced in dehydrogenation processes of butane to butene and butene to butadiene by condensing water using an evaporator. A drawback of this conventional method is that heavy hydrocarbons are not evaporated and form a hydrocarbon layer on top of evaporating water and eventually cause fouling of the heat exchange surface in the boiler and potential slugs of vaporized hydrocarbon. The conversion of butane to butene and butene to butadiene is limited by equilibrium and positive free energy is formed by dehydrogenation reactions of butane to butene followed by butene to butadiene. The direct dehydrogenation reactions are endothermic and require additional heat input to drive the reaction. Direct dehydrogenation is slightly favorable only at high temperatures of about 700° C. There is also a low butadiene yield by this method, as in the catalytic dehydrogenation of n-butane predominantly 1-butene and 2-butene are formed.

The present subject matter provides a method of conversion of butenes to butadiene by oxidative dehydrogenation. This method is not limited by equilibrium and there is negative free energy formed over a wide range of temperatures by oxidative dehydrogenation reaction. The present subject matter advantageously provides a means to attain high conversion of mixed butane/butene feed to butadiene in a single pass. An additional benefit of the present subject matter is by first converting butenes to butadiene without the formation of byproduct hydrogen, oxidative dehydrogenation effluent may be sent directly to direct dehydrogenation as there is little or no hydrogen in the effluent stream. Since the effluent from oxidative dehydrogenation is at high temperature, the additional heating requirement is only marginal to drive the endothermic dehydrogenation reaction. Therefore, there is increased butadiene yield and conversion of butanes to butenes in the product stream.

A general understanding of the process for the process for the production of butadiene can be obtained by reference to the FIGURE. The FIGURE has been simplified by the deletion of a large number of apparatuses customarily employed in a process of this nature, such as vessel internals, temperature and pressure controls systems, flow control valves, recycle pumps, etc. which are not specifically required to illustrate the performance of the invention. Furthermore, the illustration of the process of this invention in the embodiment of a specific drawing is not intended to limit the invention to specific embodiments set out herein.

The present invention, as shown in the FIGURE, includes passing a feed stream in line 10 comprising butanes and butenes to an oxidative dehydrogenation reaction unit 100 to generate an effluent stream comprising butanes, butenes and butadiene. The feed stream is passed along with steam in line 20 and an oxygen containing stream in line 30 to the oxidative dehydrogenation reaction unit 100. The oxidative dehydrogenation reaction unit design is flexible and can process a wide variety of feeds. Unlike the direct dehydrogenation processes, in which conversion is limited by the equilibrium concentrations of the products and feed, the oxidative dehydrogenation reaction proceeds essentially to completion. The conversion in each reactor unit may be adjusted by increasing or decreasing the amount of oxygen feed.

There may be excess butene in the feed stream in line 10 to consume all the oxygen and to minimize the residence time of oxygen. Reactor temperature can also limit the feasible conversion per pass. The reactor effluent temperatures increase rapidly as the reactions progress. The feed steam serves partly to control the reactor outlet temperature; the steam absorbs a large part of the heat of reaction. The oxidative dehydrogenation reaction unit 100 is operated at oxidative dehydrogenation operating conditions to generate an effluent stream in line 40. The oxidative dehydrogenation reactions are exothermic and have a high initiation temperature. The oxidative dehydrogenation reaction unit 100 may be operated adiabatically at a pressure of about 0.1 MPa (g) to about 0.3 MPa (g), and at an inlet temperature ranging from about 300° C. to about 400° C. The oxygen feed, steam feed and the inlet temperature control the temperature of the reactor unit 100. Lower pressure operation is desired to avoid polymerization and coking of the product olefins, diolefins, and acetylene. The oxidative dehydrogenation reaction unit 100 is operated to have the effluent stream leave the unit at a temperature about 300° C. to about 600° C. and preferably at a temperature of about 500° C. to about 600° C. The oxidative dehydrogenation reaction unit 100 is operated to have the effluent stream leave the unit at a pressure of about 100 kPa to about 500 kPa and preferably at a pressure of about 100 kPa to about 300 kPa. The catalysts used for oxidative dehydrogenation reaction in the oxidative dehydrogenation reaction unit 100 may be selected from the group consisting of ferrite-based catalysts and molybdenum bismuth catalysts. The ferrite based catalysts with iron and oxygen may contain at least one compound selected from the group consisting of Cu, Al, Cr, Ti, V, Mo, W, Na, Li, K, Sn, Pb, Sb, Bi, Ga, rare earth elements and mixtures thereof which is capable of forming a crystalline structure with iron and oxygen. The catalysts selected are designed such that any byproduct formation favors the relatively benign byproduct CO2.

The oxidative dehydrogenation reaction unit 100 may comprise two or more staged reactor beds. The two-stage reactor can be designed to minimize butadiene loss and, by virtue of much higher yield, result in higher overall plant efficiency. There may be intercooling between the staged reactor beds of oxidative dehydrogenation reaction unit 100 to reduce the required steam. The ratio of butanes to butenes is about 0.1 to 1.0. The molar ratio of oxygen to butene is about 0.5 to 1.3. The molar ratio of steam to butene is about 5 to 15 and preferably in the range of about 9 to 14.

The effluent stream from the oxidative dehydrogenation reaction unit 100 in line 40 is passed to a dehydrogenation reaction unit 200 to generate a process stream comprising butadiene. The effluent stream in line 40 may be heated before passing the effluent stream to the dehydrogenation reaction unit 200. The effluent stream in line 40 may be heated to a temperature of about 600° C. to about 700° C. The effluent stream in line 40 from oxidative dehydrogenation reaction unit 100 may be diluted with oxygen before passing the effluent to the dehydrogenation reaction unit 200 to maximize the butene conversion. The splitting of oxygen containing stream between the oxidative dehydrogenation reaction unit and dehydrogenation reaction unit enables limiting the exotherm in each reaction unit that can reduce the overall steam requirement for the process.

The effluent stream in line 40 is dehydrogenated over a dehydrogenation catalyst to produce a product stream comprising butadiene in line 50. The dehydrogenation unit 200 is operated at dehydrogenation operating conditions to generate a process effluent stream comprising butadiene in line 50. The reactor effluent in line 50 may be sent to a Quench Tower (not shown), to condense both the dilution steam added to the feed and the additional water vapor generated via the oxidative reactions. Condensed water is recovered and vaporized to provide all of the reactor steam requirements. The hot reactor effluent in line 50 contains high quality sensible heat that may be recovered. The effluent stream in line 50 from the dehydrogenation unit 200 is passed to a heat and product recovery unit 300 to generate a crude C4 product stream in line 90. The utilities for steam generation are minimized by using heat and product recovery unit. The light gases are recovered at the top of the heat and product recovery unit 300 in line 60. The heavy hydrocarbons and water may be recovered at the bottom of the heat and product recovery unit 300 in lines 70 and 80 respectively. The net water produced by the process may be sent to water treatment (not shown). The crude C4 product stream in line 90 comprising butadiene may be sent to an extractive distillation unit (not shown) to produce high-purity butadiene. The overall yield of butadiene by the process is about 86 wt %.

The reactor units may be arranged in a series format, and can be positioned in any convenient manner, in particular in a manner that facilitates the transfer of reactants between reactor units, and provides for access to admit flows or withdraw process streams.

The present invention can utilize fixed bed reactors, fluidized bed reactors or moving bed reactors. A preferred mode is for the use of moving bed reactors, with fresh catalyst passed to the first reactor unit. The catalyst from the first reactor may be passed to the second reactor. The process can further include reactor units which comprise a plurality of reactor beds.

Operating conditions for the dehydrogenation reaction unit may include an operating temperature in the range of from 500° C. to about 700° C., an operating pressure from 100 kPa to about 450 kPa (absolute) and a liquid hourly space velocity of from about 0.5 to about 50. The preferred operating temperature will be within the range of from about 540° C. to 660° C., and the preferred operating pressure is about 100 kPa to about 250 kPa (absolute). A more preferred operating condition include a temperature of about 580° C. to about 645° C., an operating pressure of about 100 kPa to about 170 kPa (absolute). The dehydrogenation reaction temperature is about 25° C. above the oxidative dehydrogenation reaction effluent temperature up to 700° C. The temperature can be controlled by the flow of steam to the reactor units.

The preferred dehydrogenation catalyst is comprised of a Group VIII metal, and preferably a platinum group component, preferably platinum, a tin component and an alkali metal component with a porous inorganic carrier material. Another metal that can be used is chromium. Other catalytic compositions may be used within this zone if desired. The preferred catalyst contains an alkali metal component chosen from cesium, rubidium, potassium, sodium and lithium. The preferred alkali metal is normally chosen from cesium and potassium. Preferred dehydrogenation catalysts comprise an alkali metal and a halogen such as potassium and chlorine in addition to the tin and platinum group components. The preparation and use of dehydrogenation catalysts is well known to those skilled in the art and further details as to suitable catalyst compositions are available in patents, such as those cited above, and other standard references (U.S. Pat. Nos. 4,486,547 and 4,438,288).

While the invention has been described with what are presently considered the preferred embodiments, it is to be understood that the invention is not limited to the disclosed embodiments, but it is intended to cover various modifications and equivalent arrangements included within the scope of the appended claims.

SPECIFIC EMBODIMENTS

While the following is described in conjunction with specific embodiments, it will be understood that this description is intended to illustrate and not limit the scope of the preceding description and the appended claims.

A first embodiment of the invention is a process for the production of butadiene, comprising passing a feed stream comprising butanes and butenes to an oxidative dehydrogenation reaction unit to generate an effluent stream comprising butanes, butenes and butadiene; and passing the effluent stream to a dehydrogenation unit to generate a process stream comprising butadiene. An embodiment of the invention is one, any or all of prior embodiments in this paragraph up through the first embodiment in this paragraph further comprising passing steam and an oxygen containing stream along with the feed stream to the oxidative dehydrogenation reaction unit. An embodiment of the invention is one, any or all of prior embodiments in this paragraph up through the first embodiment in this paragraph further comprising passing the process stream to a heat and product recovery unit to generate a crude C4 product stream. An embodiment of the invention is one, any or all of prior embodiments in this paragraph up through the first embodiment in this paragraph wherein the oxidative dehydrogenation reaction unit comprises two or more staged reactor beds. An embodiment of the invention is one, any or all of prior embodiments in this paragraph up through the first embodiment in this paragraph wherein the butanes to butenes ratio is between 0.1 and 1.0. An embodiment of the invention is one, any or all of prior embodiments in this paragraph up through the first embodiment in this paragraph wherein the oxidative dehydrogenation reaction unit is operated to have the effluent stream leave the unit at a temperature about 300° C. to about 600° C. An embodiment of the invention is one, any or all of prior embodiments in this paragraph up through the first embodiment in this paragraph further comprising heating the effluent stream before passing the effluent stream to the dehydrogenation unit. An embodiment of the invention is one, any or all of prior embodiments in this paragraph up through the first embodiment in this paragraph wherein the effluent stream is heated to a temperature of about 600° C. to about 700° C. An embodiment of the invention is one, any or all of prior embodiments in this paragraph up through the first embodiment in this paragraph wherein heat is recovered from the process stream. An embodiment of the invention is one, any or all of prior embodiments in this paragraph up through the first embodiment in this paragraph wherein the oxidative dehydrogenation reaction unit is operated to have the effluent stream leave the unit at a pressure of about 100 kPa to about 500 kPa. An embodiment of the invention is one, any or all of prior embodiments in this paragraph up through the first embodiment in this paragraph wherein there is intercooling between the staged reactor beds of oxidative dehydrogenation reaction unit to reduce the required steam. An embodiment of the invention is one, any or all of prior embodiments in this paragraph up through the first embodiment in this paragraph wherein the molar ratio of oxygen to butene is about 0.5 to 1.3. An embodiment of the invention is one, any or all of prior embodiments in this paragraph up through the first embodiment in this paragraph wherein the molar ratio of steam to butane is about 5 to 15. An embodiment of the invention is one, any or all of prior embodiments in this paragraph up through the first embodiment in this paragraph wherein the catalyst for the oxidative dehydrogenation reaction is selected from the group consisting of ferrite-based catalysts and molybdenum bismuth catalysts. An embodiment of the invention is one, any or all of prior embodiments in this paragraph up through the first embodiment in this paragraph further comprising diluting the effluent from oxidative dehydrogenation unit with oxygen.

A second embodiment of the invention is a process for the production of butadiene comprising passing a feed stream comprising butanes and butenes to an oxidative dehydrogenation reaction unit to generate an effluent stream comprising butanes, butenes and butadiene; passing steam and oxygen along with the feed stream to the oxidative dehydrogenation reaction unit; passing the effluent stream to a dehydrogenation unit to generate a process stream comprising butadiene; and passing the process stream to a heat and product recovery unit to generate a crude C4 product stream. An embodiment of the invention is one, any or all of prior embodiments in this paragraph up through the second embodiment in this paragraph wherein the oxidative dehydrogenation reaction unit comprises two or more staged reactor beds. An embodiment of the invention is one, any or all of prior embodiments in this paragraph up through the second embodiment in this paragraph further comprising heating the effluent stream before passing the effluent stream to the dehydrogenation unit to a temperature of about 600° C. to about 700° C. An embodiment of the invention is one, any or all of prior embodiments in this paragraph up through the second embodiment in this paragraph wherein there is intercooling between the staged reactor beds of oxidative dehydrogenation reaction unit to reduce the required steam. An embodiment of the invention is one, any or all of prior embodiments in this paragraph up through the second embodiment in this paragraph wherein the oxidative dehydrogenation reaction unit is operated to have the effluent stream leave the unit at a temperature about 300° C. to about 600° C. and a pressure of about 100 kPa to about 500 kPa.

Without further elaboration, it is believed that using the preceding description that one skilled in the art can utilize the present invention to its fullest extent and easily ascertain the essential characteristics of this invention, without departing from the spirit and scope thereof to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

The invention claimed is:

1. A process for producing butadiene, comprising:
passing a feed stream comprising n-butane and n-butenes to an oxidative dehydrogenation reaction unit comprising an oxidative dehydrogenation catalyst to generate an effluent stream comprising n-butane, n-butenes and butadiene, wherein the oxidative dehydrogenation reaction unit is operated to have the effluent stream leave the oxidative dehydrogenation reaction unit at a temperature about 300° C. to about 600° C.;
heating the effluent stream to a temperature of about 600° C. to about 700° C.; and
passing the effluent stream to a direct dehydrogenation unit comprising a dehydrogenation catalyst to generate a process stream comprising butadiene.

2. The process of claim 1 further comprising passing steam and an oxygen containing stream along with the feed stream to the oxidative dehydrogenation reaction unit.

3. The process of claim 2 wherein a molar ratio of oxygen to butene is about 0.5 to 1.3.

4. The process of claim 2 wherein a molar ratio of steam to n-butane is about 5 to 15.

5. The process of claim 2 further comprising diluting the effluent from the oxidative dehydrogenation unit with oxygen.

6. The process of claim 1 further comprising passing the process stream to a heat and product recovery unit to generate a crude C4 product stream.

7. The process of claim 1 wherein the oxidative dehydrogenation reaction unit comprises two or more staged reactor beds.

8. The process of claim 7 wherein there is intercooling between the staged reactor beds of oxidative dehydrogenation reaction unit.

9. The process of claim 1 wherein a n-butane to n-butene ratio is between 0.1 and 1.0.

10. The process of claim 1 further comprising heating the effluent stream before passing the effluent stream to the dehydrogenation unit.

11. The process of claim 1 wherein heat is recovered from the process stream.

12. The process of claim 1 wherein the oxidative dehydrogenation reaction unit is operated to have the effluent stream leave the oxidative dehydrogenation reaction unit at a pressure of about 100 kPa to about 500 kPa.

13. The process of claim 1 wherein the oxidative dehydrogenation catalyst for the oxidative dehydrogenation reaction is selected from the group consisting of ferrite-based catalysts and molybdenum bismuth catalysts.

14. A process for producing butadiene, comprising:
passing a feed stream comprising n-butane and n-butenes to an oxidative dehydrogenation reaction unit comprising an oxidative dehydrogenation catalyst to generate an effluent stream comprising n-butane, n-butenes and butadiene, wherein the oxidative dehydrogenation reaction unit is operated to have the effluent stream leave the oxidative dehydrogenation reaction unit at a temperature about 300° C. to about 600° C.;
passing steam and oxygen along with the feed stream to the oxidative dehydrogenation reaction unit;
heating the effluent stream to a temperature of about 600° C. to about 700° C.;
passing the effluent stream to a direct dehydrogenation unit comprising a dehydrogenation catalyst to generate a process stream comprising butadiene; and
passing the process stream to a heat and product recovery unit to generate a crude C4 product stream.

15. The process of claim 14 wherein the oxidative dehydrogenation reaction unit comprises two or more staged reactor beds.

16. The process of claim 15 wherein there is intercooling between the staged reactor beds of oxidative dehydrogenation reaction unit.

17. The process of claim 14 further comprising heating the effluent stream before passing the effluent stream to the dehydrogenation unit to a temperature of about 600° C. to about 700° C.

18. The process of claim 14 wherein the oxidative dehydrogenation reaction unit is operated to have the effluent stream leave the oxidative dehydrogenation reaction unit at a pressure of about 100 kPa to about 500 kPa.

* * * * *